(12) United States Patent
Van Der Linde et al.

(10) Patent No.: US 10,561,467 B2
(45) Date of Patent: Feb. 18, 2020

(54) INTERVENTIONAL APPARATUS FOR PERFORMING AN INTERVENTIONAL PROCEDURE

(71) Applicant: KONINKLIJKE PHILIPS N.V., Eindhoven (NL)

(72) Inventors: Franciscus Reinier Antonius Van Der Linde, Schijndel (NL); Franciscus Johannes Gerardus Hakkens, Eersel (NL); Cornelis Gerardus Maria De Haas, Nuenen (NL); Cornelius Antonius Nicolaas Maria Van Der Vleuten, Liempde (NL); Adrianus Wilhelmus Dionisius Maria Van Den Bijgaart, Helvoirt (NL); Maurice Hubertus Elisabeth Van Der Beek, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 8 days.

(21) Appl. No.: 15/510,022

(22) PCT Filed: Sep. 6, 2015

(86) PCT No.: PCT/EP2015/070308
§ 371 (c)(1),
(2) Date: Mar. 9, 2017

(87) PCT Pub. No.: WO2016/041792
PCT Pub. Date: Mar. 24, 2016

(65) Prior Publication Data
US 2017/0304010 A1 Oct. 26, 2017

(30) Foreign Application Priority Data
Sep. 16, 2014 (EP) .................................... 14184901

(51) Int. Cl.
*A61B 34/20* (2016.01)
*A61B 1/018* (2006.01)
*A61B 17/00* (2006.01)

(52) U.S. Cl.
CPC .............. *A61B 34/20* (2016.02); *A61B 1/018* (2013.01); *A61B 17/00234* (2013.01);
(Continued)

(58) Field of Classification Search
CPC ... A61B 34/20; A61B 17/00234; A61B 1/018; A61B 2017/0034; A61B 2034/2061; A61B 2017/00469
See application file for complete search history.

(56) References Cited

U.S. PATENT DOCUMENTS 4,421,106 A 12/1983 Uehara
5,254,088 A 10/1993 Lundquist et al.
(Continued)

FOREIGN PATENT DOCUMENTS

JP WO 2014057853 A1 * 4/2014 ......... G02B 23/2476

*Primary Examiner* — Bo Joseph Peng

(57) ABSTRACT

The invention relates to an interventional apparatus comprising an interventional device with a handle (6). The handle comprises a) a first guide (20, 51) guiding an optical fiber, which is also guided within the interventional device, from a first proximal opening (14) of the handle to a distal portion (21) of the handle, wherein the first guide only has radii of curvature being larger than 10 mm, and b) a second guide (22) for guiding an elongated interventional instrument from a second proximal opening (13) of the handle to the distal portion of the handle. Since the first guide is relatively straight, the optical fiber is substantially not bent or only slightly bent and the likelihood that the interventional instrument and the optical fiber press against each other can be significantly reduced. This allows for an improved accuracy of determining the position of the interventional device by optical shape sensing.

20 Claims, 6 Drawing Sheets

(52) U.S. Cl.
CPC ............... *A61B 2017/0034* (2013.01); *A61B 2017/00469* (2013.01); *A61B 2034/2061* (2016.02)

(56) References Cited

U.S. PATENT DOCUMENTS

| | | | |
|---|---|---|---|
| 5,395,316 | A | 3/1995 | Martin |
| 5,715,817 | A | 2/1998 | Stevens-Wright et al. |
| 5,855,577 | A | 1/1999 | Murphy-Chutorian et al. |
| 5,910,105 | A | 6/1999 | Swain et al. |
| 7,141,050 | B2 | 11/2006 | Deal et al. |
| 8,298,135 | B2 | 10/2012 | Ito et al. |
| 9,144,368 | B2 | 9/2015 | Kubo |
| 9,417,057 | B2 | 8/2016 | 'T Hooft et al. |
| 2001/0037084 | A1 | 11/2001 | Nardeo |
| 2005/0272975 | A1* | 12/2005 | McWeeney ........ A61B 1/00071 600/113 |
| 2006/0030753 | A1 | 2/2006 | Boutillette et al. |
| 2007/0299423 | A1 | 12/2007 | Jones et al. |
| 2010/0016655 | A1 | 1/2010 | Annest et al. |
| 2010/0069760 | A1 | 3/2010 | Tang |
| 2012/0136207 | A1 | 5/2012 | Goldfarb et al. |
| 2013/0028554 | A1 | 1/2013 | Wong et al. |
| 2015/0208947 | A1 | 7/2015 | Tojo |
| 2015/0272472 | A1 | 10/2015 | Cathier et al. |

\* cited by examiner

INTERVENTIONAL APPARATUS FOR PERFORMING AN INTERVENTIONAL PROCEDURE

CROSS-REFERENCE TO PRIOR APPLICATIONS

This application is the U.S. National Phase application under 35 U.S.C. § 371 of International Application Serial No. PCT/EP2015/070308, filed on Sep. 6, 2015, which claims the benefit of European Patent Application No. 14184901.8, filed on Sep. 16, 2014. These applications are hereby incorporated by reference herein.

FIELD OF THE INVENTION

The invention relates to an interventional apparatus for performing an interventional procedure and a position determination method for determining the position of an elongated interventional device of the interventional apparatus.

BACKGROUND OF THE INVENTION

U.S. Pat. No. 4,421,106 discloses a fiber scope for biopsical use which is designed to be operable by a single operator and which comprises a forceps, an adapter for selectively controlling a motion of tip ends of the forceps, and a stopper adapted to selectively fix a longitudinal motion of a forceps controlling wire. The adapter is disposed at or adjacent to an inlet portion of a forceps guide sleeve.

US 2006/0030753 A1 discloses a steerable imaging catheter comprising an elongated catheter tube having a proximal end and a distal end, at least one steering cable extending along the catheter tube substantially from the proximal end to the distal end of the catheter tube to control the movement of the distal end of the catheter tube, and an imaging fiber optic cable having a proximal end and a distal end. The imaging fiber optic cable extends along the catheter tube substantially from the proximal end to the distal end of the catheter tube and transmits illumination light from its proximal end to its distal end and an image from its distal end to its proximal end.

US 2001/0037084 A1 discloses a steerable medical catheter comprising a polymeric main shaft having first and second ends with a plurality of lumens extending longitudinally therethrough and a shaft tip portion comprising a metallic coil spring with a polymeric coating having first and second ends. The first end of the metallic coil spring is fused to the second end of the main shaft and the polymeric coating has an inner portion configured to define a plurality of lumens between the first and second ends of the coil spring which extend through the coil spring. The lumens through the coil spring are aligned with the lumens in the main shaft such that the lumens extend through the catheter, wherein the metallic coil spring is fully encapsulated by the polymeric coating and the second end of the main shaft. The medical catheter further comprises a first control wire located in one of the lumens having a first end which terminates in proximity to the second end of the coil spring and a second end which extends from the first end of the main shaft.

WO 2004/035125 A1 discloses a catheter comprising a shaft having a proximal end, a distal end and a wire guide lumen extending through the shaft. The catheter further comprises a plurality of intermediate wire guide access ports through a side wall of the shaft for providing access to the wire guide lumen, wherein the intermediate wire guide access ports are located between and spaced apart from the proximal and distal ends. The catheter is adapted for use with an endoscope having a working channel extending between a distal port and a proximal port, wherein the plurality of intermediate wire guide access ports are accessible outside the endoscope when the catheter is positioned through the working channel such that the distal end of the catheter and the distal port of the working channel are substantially aligned.

WO 98/46143 discloses a control handle that is detachably connected to a proximal end of an endoscope and that has several telescoping components that may be sequentially operated, first to pass a needle through tissue and then to eject a retainer tag and attached suture end from a distal end of the needle. The control handle includes first and second longitudinally movable slides, wherein one slide is connectable to a proximally extending end of a tubular needle shaft and the other slide is attachable to a proximally extending end of an injector wire that is slidably movable through the needle shaft. The distal end of the handle is detachably connectable to a biopsy fitting that is disposed at a proximal end of the endoscope.

WO 2014/091418 A1 discloses a position determination apparatus for determining the position of a working element, which is arranged within an object having an inner structure, with respect to a model of the object. The position determination apparatus comprises a) a position and shape providing unit for providing the position and shape of a registration element within the inner structure of the object and a spatial relation between the working element and the registration element, b) a model providing unit for providing the model of the object, c) a transformation determination unit for determining a transformation relating the inner structure of the model and the position and shape of the registration element with respect to each other such that the inner structure of the model corresponds to the provided position and shape of the registration element, and d) a position determination unit for determining the position of the working element with respect to the model depending on the spatial relation between the working element and the registration element and the determined transformation.

US 2010/0016655 A1 discloses an introducer for treating a heart of a patient. The introducer comprises an introducer shaft extending between a proximal end and a distal end, wherein the distal end has a tissue penetrating tip such that the shaft is insertable through first and second heart walls bordering a chamber of the heart.

CN 103945754 A discloses an endoscope including an insertion portion, an operation portion and a universal cable. The operation portion comprises an operation portion main body which is a first sheath body and a grasping portion case body which is a second sheath body. The operation portion main body is provided with a bending operation apparatus, an air/water feeding button and a suction button. The grasping portion case body is provided with a treatment instrument insertion port.

In interventional procedures a steerable catheter may be used for delivering a guide wire and/or other interventional instruments to a target location, wherein the position of the steerable catheter and the guide wire and/or the other interventional instruments may be determined by optical shape sensing. Optical shape sensing requires an optical fiber to be arranged within the steerable catheter together with the guide wire and/or the other interventional instruments such that several elongated elements are used, which are translated and/or rotated during the interventional procedure and which entangle and press against each other, which likely leads to a disruption of the optical shape sensing determination of the position of the steerable catheter and hence of the guide wire and/or the other interventional instruments.

SUMMARY OF THE INVENTION

It is an object of the present invention to provide an interventional apparatus for performing an interventional procedure and a position determination method for determining the position of an elongated interventional device of the interventional apparatus, which allow for an improved accuracy of the position determination.

In a first aspect of the invention an interventional apparatus for performing an interventional procedure is presented, wherein the interventional apparatus comprises:

an elongated interventional device comprising a first lumen accommodating an optical shape sensing fiber for allowing for a determination of a position of the interventional device by optical shape sensing and a second lumen for accommodating an elongated interventional instrument, a handle comprising a) a first guide for guiding the optical shape sensing fiber, which is also guided within the interventional device, from a first proximal opening of the handle to a distal portion of the handle, wherein the distal portion of the handle is adapted to be connected to a proximal portion of the interventional device, wherein the first guide only has radii of curvature being larger than 10 mm, and b) a second guide for guiding an elongated interventional instrument from a second proximal opening of the handle to the distal portion of the handle, wherein portions of the first guide and the second guide close to the first proximal opening and the second proximal opening are parallel to each other, and an optical shape sensing device for determining the position of the elongated interventional device by optical shape sensing by using the optical shape sensing fiber, wherein the interventional device and the handle are attached to each other such that the optical shape sensing fiber is guided from the first proximal opening of the handle to the distal portion of the handle and then into the first lumen of the interventional device and such that the interventional instrument is guidable from the second proximal opening of the handle to the distal portion of the handle and then into the second lumen of the interventional device.

Since the handle comprises a first guide for guiding the optical fiber and a second guide for guiding an interventional instrument, wherein the first guide is relatively straight, i.e. only has radii of curvature being larger than 10 mm, the optical fiber is substantially not bent or only slightly bent within the handle and the likelihood that the interventional instrument and the optical fiber press against each other within the handle can be significantly reduced. This allows for an improved accuracy of determining the position of the optical fiber and hence the position of the interventional device.

In a preferred embodiment the first guide within the handle only has radii of curvature being larger than 30 mm, further preferred larger than 50 mm and even further preferred larger than 100 mm. Especially if the first guide within the handle only has radii of curvature being larger than 100 mm, the optical fiber is substantially not bent and the likelihood that the interventional instrument and the optical fiber press against each other within the handle can be further reduced, thereby allowing for a further improved accuracy of determining the position of the optical fiber and hence the position of the interventional device.

The second guide is preferentially adapted to guide a guide wire as the interventional instrument. Preferentially the second guide only has radii of curvature being larger than 300 mm, i.e. preferentially also the second guide is relatively straight within the handle. Moreover, at least portions of the first guide and the second guide are preferentially substantially parallel to each other. In particular, the portions of the first guide and the second guide close to the first proximal opening and the second proximal opening, respectively, are preferentially substantially parallel to each other. This especially means that the portions of the first guide and the second guide at the proximal end of the handle are preferentially parallel to each other. If these portions are substantially parallel to each other and straight, even after having left the handle through the first and second proximal openings close to the handle the optical fiber and the interventional instrument are also substantially parallel to each other such that the likelihood of entanglement and of corresponding pressures and frictions can be further reduced, which may lead to a further increased accuracy of determining the position of the interventional device by optical shape sensing.

The first guide and/or the second guide are preferentially formed by a tube, especially by a flexible tube, extending from the respective proximal opening of the handle to the distal portion of the handle. The respective tube used for forming the first guide or the second guide, respectively, within the handle can be a single integrated tube or it can be made of several tubes connected to each other. Moreover, the respective tube forming the first guide or the second guide, respectively, within the handle can also extend to the outside of the handle, i.e. it can have an inner portion forming the first guide or the second guide, respectively, within the handle and an outer portion outside of the handle. Moreover, the interventional device may be a steerable elongated interventional device and the handle may be adapted to be connected to this steerable elongated interventional device. The steerable elongated interventional device may have a first lumen for accommodating the optical fiber and a second lumen for accommodating the interventional instrument, wherein the handle and the interventional device may be connected to each other such that the optical fiber is guidable from the first proximal opening of the handle to the distal portion of the handle and then into the first lumen of the interventional device and such that the interventional instrument is guidable from the second proximal opening of the handle to the distal portion of the handle and then into the second lumen of the interventional device. Preferentially, the handle is adapted to be connected to a steerable catheter or sheath as the elongated interventional device.

The spacing between the first proximal opening and the second proximal opening from center line to center line is preferentially within a range of 10 to 15 mm. Thus, virtual straight lines through the centers of the first and second proximal openings have preferentially a distance within a range of 10 to 15 mm. Moreover, preferentially the handle comprises an elongated body having a first proximal opening to which an elongated extension element is attached having a proximal opening forming the first proximal opening of the handle, wherein the first guide is adapted to guide the optical fiber from the proximal opening of the extension element through the proximal opening of the body to the distal portion of the handle. By using the elongated extension element the first proximal opening of the handle can be provided at a proximally further shifted position, which can lead to a further reduced likelihood of entanglement and corresponding pressures and frictions, which may lead to a further increased accuracy of determining the position of the interventional device by optical shape sensing. The extension element is preferentially made of a material being more flexible than the material of which the elongated body is made. This relatively flexible material of the extension element can allow for a gradual transition in stiffness from the relatively stiff elongated body to the first proximal opening of the handle. The relatively stiff elongated body is preferentially adapted to be held by a hand of a user, when the handle is used together with the interventional device.

The elongated body preferentially has a second proximal opening forming the second proximal opening of the handle such that the second guide guides the interventional instrument from the proximal opening of the elongated body to the distal portion of the handle. Moreover, the elongated body preferentially further has a distal opening for accommodating a distal accommodation element for accommodating the proximal portion of the interventional device. The distal accommodation element is preferentially made of a material being stiffer than the material of which the elongated extension element is made. The relatively stiff distal accommodation element can be regarded as being a mechanical anchor to mechanically anchor, position and align the interventional device to the handle.

The interventional apparatus comprises an optical shape sensing device for determining the position of the elongated interventional device by optical shape sensing by using the optical fiber. Optical shape sensing allows for an accurate determination of the position of the interventional device within a subject without requiring the use of, for instance, x-rays which may adversely affect the subject and/or a physician performing the interventional procedure.

In a preferred embodiment the longitudinal axis of the handle and the proximal portion of the interventional device are arranged in the same direction, in particular, they are arranged substantially along a same straight virtual line. Thus, the transition from the handle to the interventional device can be relatively smooth, thereby allowing for a further improved accuracy of determining the position of the interventional device by optical shape sensing.

In a further aspect of the invention a position determination method for determining the position of the elongated interventional device of the interventional apparatus as defined in claim 1 is presented, wherein the position determination method comprises determining the position by optical shape sensing by using the optical shape sensing device and the optical fiber guided from the first proximal opening of the handle to the distal portion of the handle and then into the first lumen of the interventional device.

It shall be understood that the interventional apparatus of claim 1 and the position determination method of claim 12 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
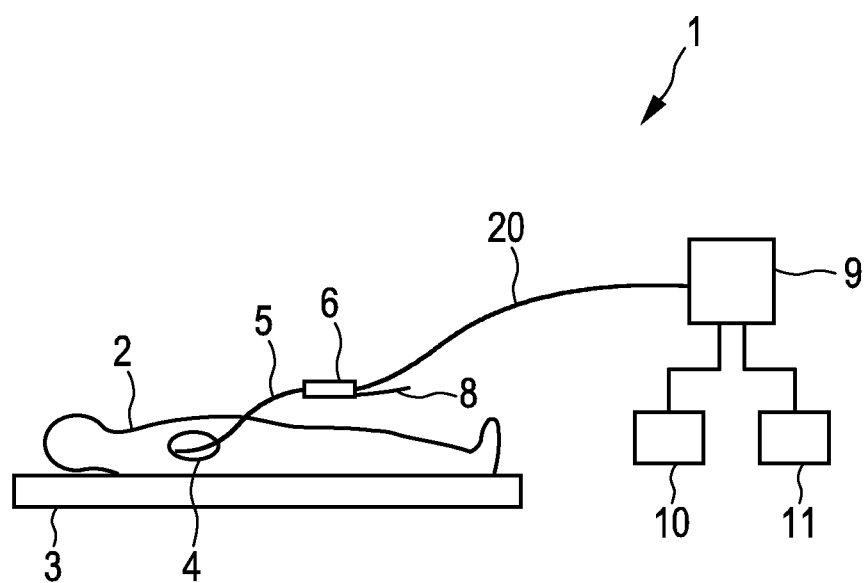
FIG. 1 shows schematically and exemplarily an embodiment of an interventional apparatus for performing an interventional procedure.

FIG. 1 shows schematically and exemplarily an embodiment of an interventional apparatus for performing an interventional procedure. The interventional apparatus 1 comprises an elongated interventional device 5 comprising several lumina. A section view of the interventional device 5 is schematically and exemplarily shown in FIG. 2.

Figure 2:
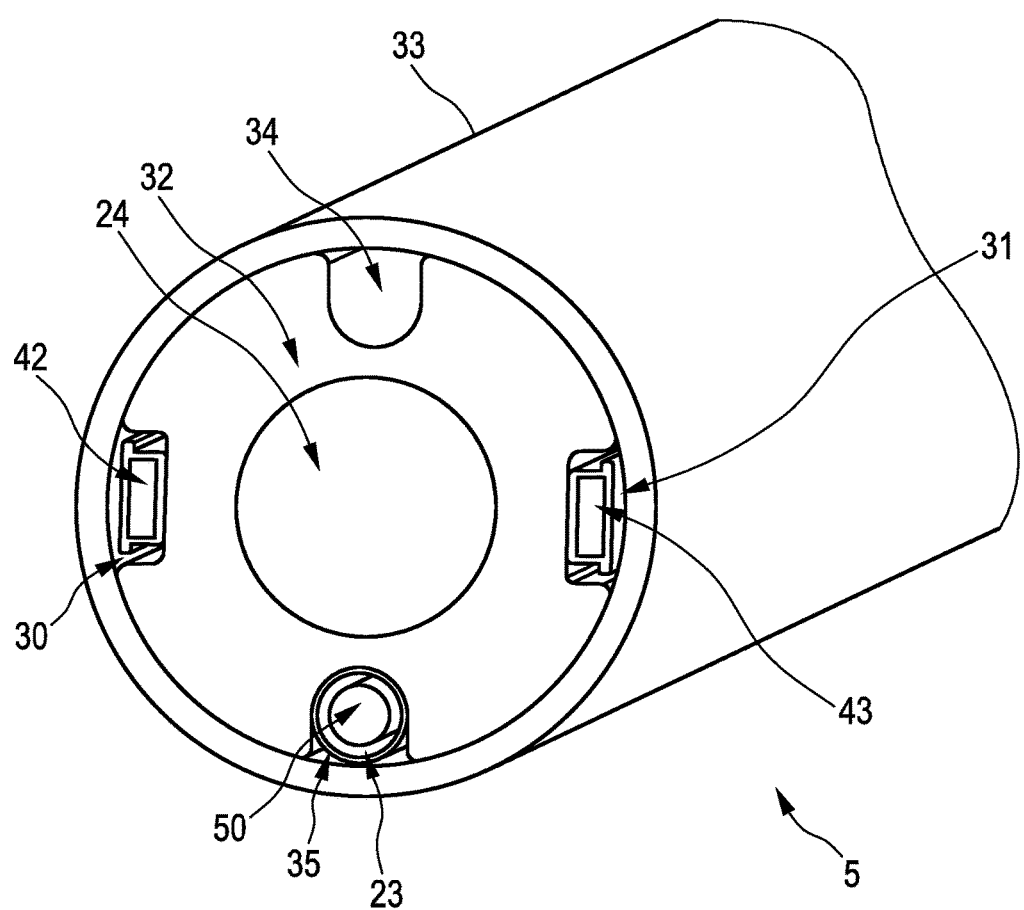
FIG. 2 shows schematically and exemplarily inner lumina of an embodiment of the interventional device of the interventional apparatus.

As can be seen in FIG. 2, the interventional device 5 comprises several lumina 23, 24, 30, 31, 34, wherein a first lumen 23 comprises a tube 35 for guiding an optical fiber 50 within the interventional device 5 and a central lumen 24 is used for guiding an interventional instrument like a guide wire. In the lumina 30, 31 pull wires 42, 43 are provided. The pull wires 42, 43 may be made of metal or a polymer. They may comprise a liner to reduce friction when being moved within the lumina 30, 31. The interventional device 5 is formed of an outer tube 33 and an inner cylinder like element 32. The outer tube 33 and the inner cylinder like element 32 may be made of thermoplastic elastomers like polyethylene (PE), Nylon (polyamide, PA), polyether block amide (PEBAx), polyurethane (PU) or others.

The optical fiber 50 is an optical shape sensing fiber, which is adapted to determine the position of the elongated interventional device 5 by optical shape sensing by using an optical shape sensing device 9. For determining the position of the interventional device 5 by optical shape sensing known optical shape sensing techniques can be used like the techniques disclosed in WO 2013/136247 A1, which is herewith incorporated by reference.

In this embodiment the elongated interventional device 5 is a steerable catheter and the interventional instrument 8 is a guide wire. In other embodiments the interventional apparatus can comprise another interventional device like another steerable interventional device such as a steerable sheath or a non-steerable interventional device like a simple catheter. Moreover, instead of the guide wire another interventional instrument may be used like an endoscope, a needle, a catheter or another elongated medical device. The elongated interventional device 5 has been inserted into a person 2 lying on a support means 3 like a table. The interventional device 5 may have been inserted, for instance, into the heart 4 of the person 2.

Figure 3:
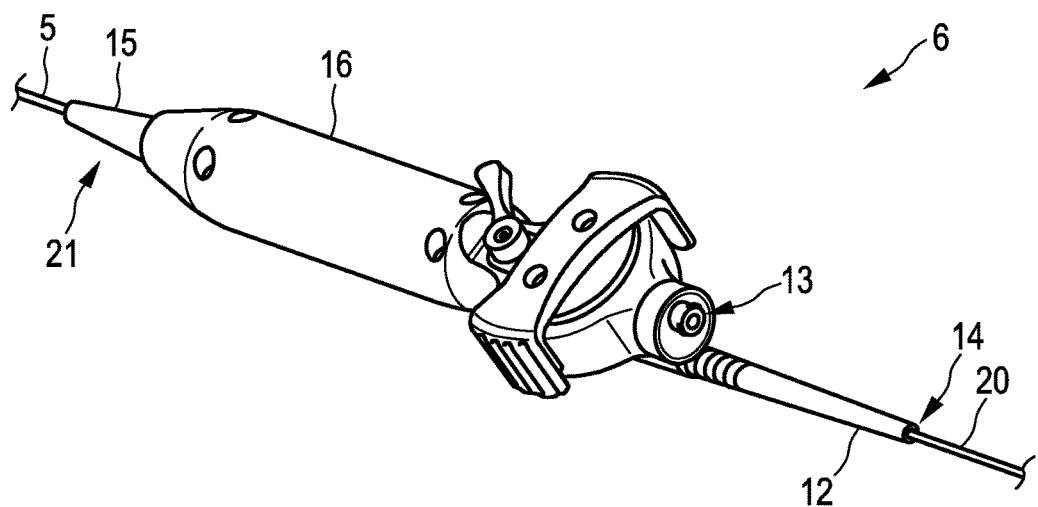
FIG. 3 shows schematically and exemplarily the exterior of an embodiment of a handle for the interventional device.

The interventional apparatus 1 further comprises a handle 6. The exterior of the handle 6 is schematically and exemplarily illustrated in more detail in FIG. 3 and the interior of the handle 6 is illustrated in more detail in FIGS. 4 to 8.

The handle 6 comprises a first guide for guiding the optical fiber 50, which is also guided within the tube 35 within the first lumen 23 of the interventional device 5, from a first proximal opening 14 of the handle to a distal portion 21 of the handle 6, wherein the distal portion 21 of the handle 6 is adapted to accommodate a proximal portion of the interventional device 5 and wherein in this embodiment the first guide only has radii of curvature within the handle 6 being larger than 100 mm. In other embodiments the first guide can also have smaller radii of curvature which are larger than 10 mm. In this embodiment the first guide is formed by a first tube 20 and a second tube 51 which are connected via an interface element 52, wherein the second tube 51 is hold by a ring-like holding element 53. In other embodiments the first guide may also be formed in another way. For instance, a single tube may be provided within the handle 6 for forming the first guide.

The handle 6 further comprises a second guide 22 for guiding an elongated interventional instrument 8 being, in this embodiment, a guide wire from a second proximal opening 13 of the handle 6 to the distal portion 21 of the handle 6. The second guide 22 only has radii of curvature within the handle 6 being larger than 300 mm. The second guide 22 is formed by a tube extending from the second proximal opening 13 of the handle 6 to the distal portion 21 of the handle 6. In this embodiment the second guide 22 and the inner element 32 of the catheter 5 are integrated, i.e. the inner element 32 also runs through the handle 6 and forms thereby the second guide 22. In other embodiments the second guide and the inner element of the catheter may not form an integrated element.

The handle 6 is connected to the steerable catheter 5 such that the optical fiber 50 is guided from the first proximal opening 14 of the handle 6 to the distal portion 21 of the handle 6 and then into the first lumen 23 of the steerable catheter 5 and such that the interventional instrument 8 is guidable from the second proximal opening 13 of the handle 6 to the distal portion 21 of the handle 6 and then into the second lumen 24 of the steerable catheter 5.

Figure 4:
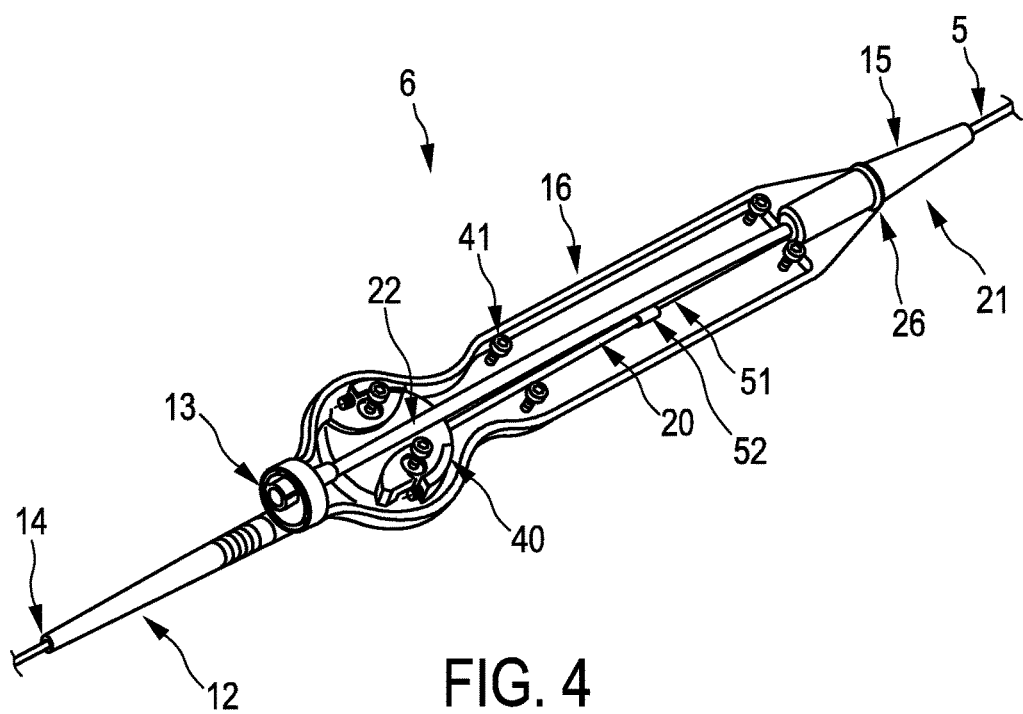
FIGS. 4 to 8 show schematically and exemplarily the interior of the embodiment of the handle.
Figure 5:
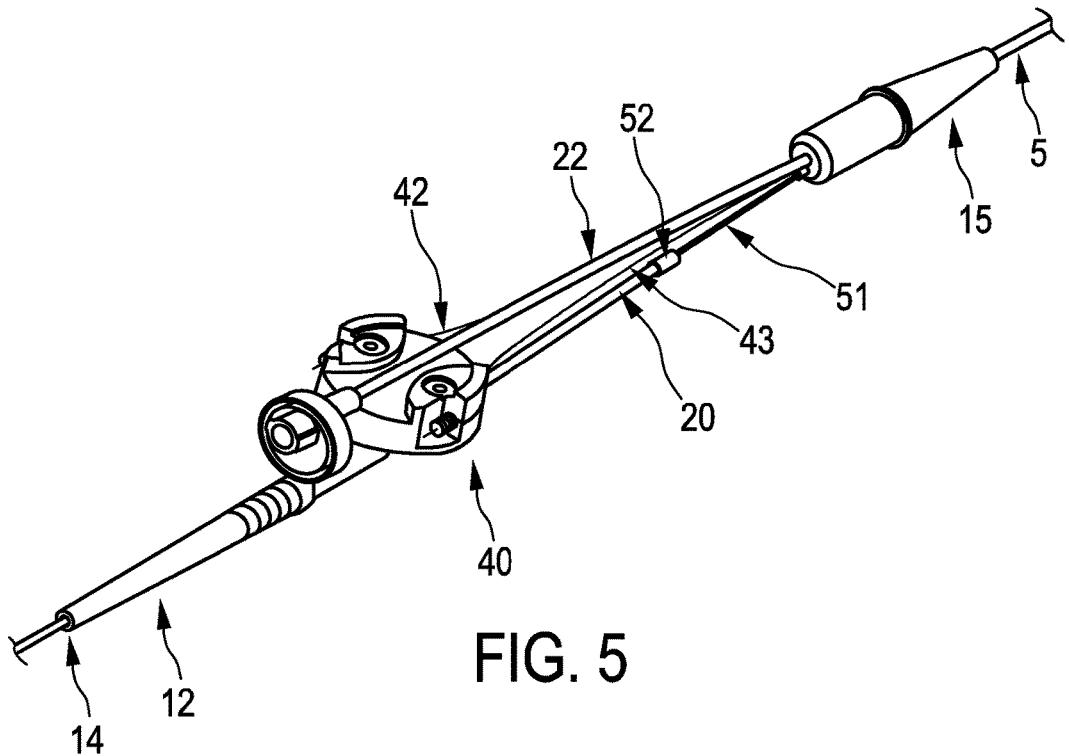
Figure 6:
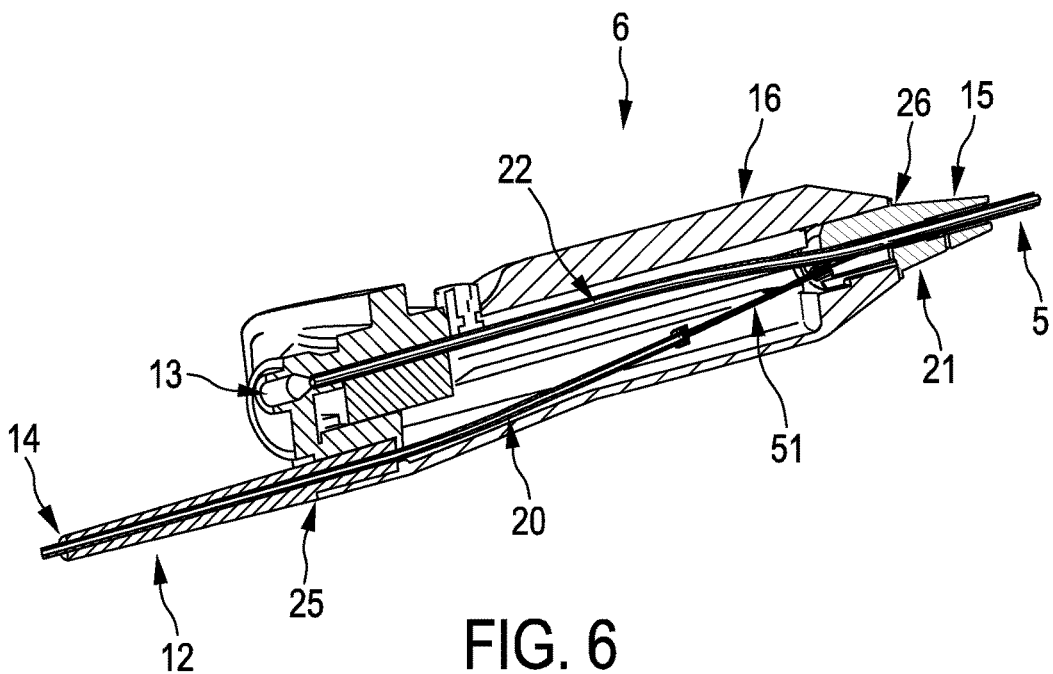
Figure 7:
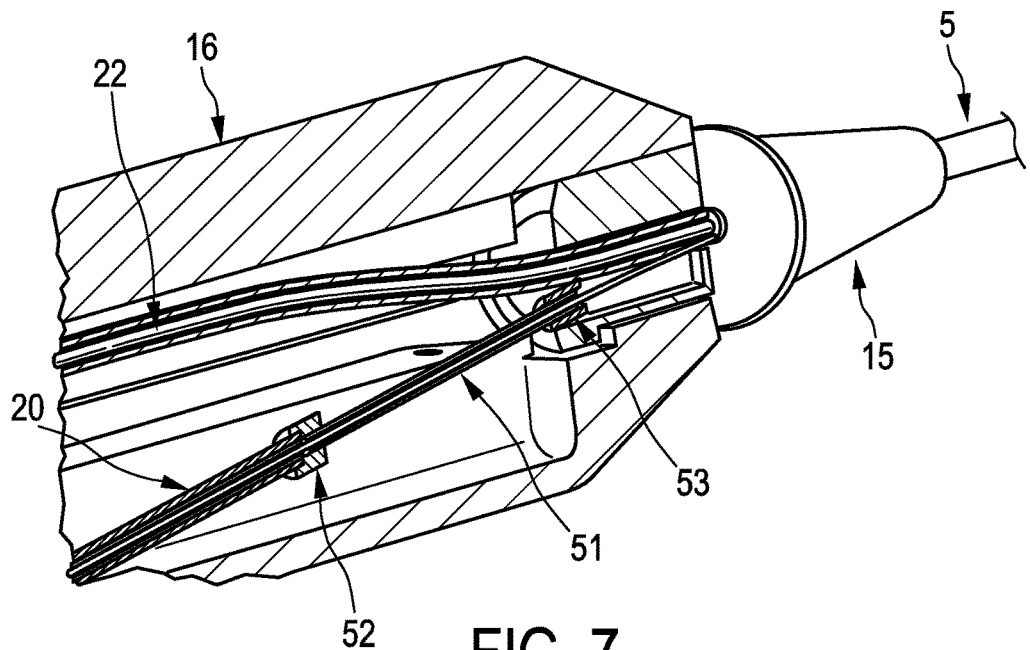
Figure 8:
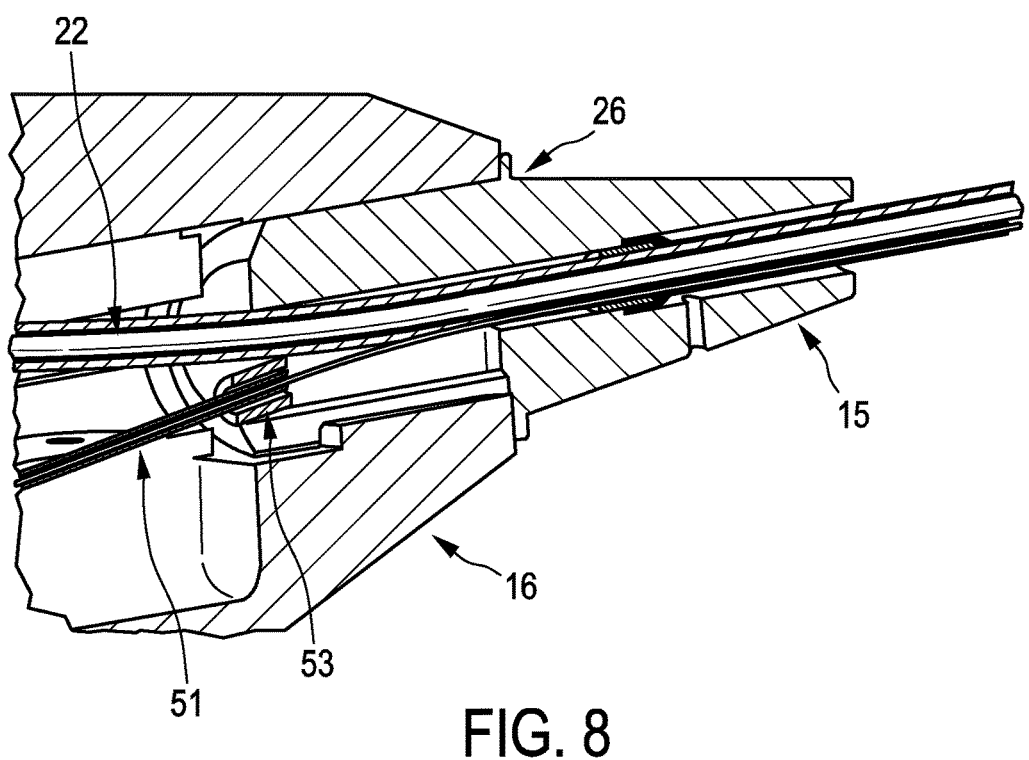

The handle 6 comprises an elongated body 16 having a first proximal opening 25 to which an elongated extension element 12 is attached having a proximal opening forming the first proximal opening 14 of the handle 6. The first guide 20, 51 is adapted to guide the optical fiber from the proximal opening 14 of the extension element 12 through the proximal opening 25 of the body 16 to the distal portion 21 of the handle 6. The elongated body 16 further comprises a second proximal opening 13 forming the second proximal opening 13 of the handle 6 such that the second guide 22 guides the interventional instrument 8 from the proximal opening 13 of the elongated body 16 to the distal portion 21 of the handle 6. Moreover, the handle 6 comprises a distal accommodation element 15, which is arranged within a distal opening 26 of the elongated body 16, for accommodating the proximal portion of the catheter 5. The extension element 12 is made of a relatively flexible material, i.e. from a material being more flexible than the materials used for manufacturing the elongated body 16 and the distal accommodation element 15. The extension element 12 can be regarded as being a mechanical support and strain relief for the first tube 20 of the first guide, especially in order to provide a gradual transition in stiffness from the relatively stiff body 16 to the proximal opening 14 of the handle 6. Outside of the handle 6, i.e. proximal from the first proximal opening 14 of the handle 6, the optical fiber may also be embedded in a tube, wherein preferentially the first tube 20 of the first guide within the handle 6 and the tube proximal of the first proximal opening 14 of the handle 6 form an integrated tube. The elongated body 16 may comprise two halves, wherein one half is illustrated in FIG. 4 and wherein screws 41 may be used for attaching the two halves to each other.

The distal accommodation element 15 can be regarded as being a mechanical anchor for mechanically anchoring, positioning and aligning the steerable catheter 5 to the handle 6. The intermediate body 16 can be regarded as being a mechanical interface to the user, wherein the outer diameter may be within a range of 20 to 30 mm, in order to easily fit inside a palm of a hand of the user. All materials of the handle 6 are preferentially cleanable and sterilizable. The exterior of the intermediate body 16 preferentially comprises a material, especially a surface texturing, which provides an improved grip to wet surgical gloves.

The steerable catheter 5 is steered by using the pull wires 42, 43 attached to an actuation mechanism 40 inside the handle 6. The distal side of each pull wire 42, 43 is attached to a ring located in the distal tip of the catheter 5. The actuation mechanism can consist of a cam that can be rotated. By rotating the cam in either direction, selectively one of the two pull wires 42, 43 is pulled. The distal tip portion of the catheter 5, which contains the ring with the pull wires attached, is preferentially more flexible than the more proximal section of the catheter 5. Pulling one of the pull wires 42, 43 will therefore result in a bending of the more flexible distal portion of the catheter 5. For more details regarding this known mechanism for steering the catheter reference is made to U.S. Pat. Nos. 5,254,088, 5,715,817 and US 2001/0037084 A1, which are herewith incorporated by reference.

The interventional apparatus 1 further comprises an input 10 like a keyboard, a touchpad, a computer mouse et cetera and an output unit 11 like a display. The input unit 10 allows the user to input commands into the optical shape sensing device 9 like a start command for starting an optical shape sensing determination or a stop command for stopping an optical shape sensing determination. The output unit 11 may be used for outputting the determined position of the steerable catheter 5 within the person 2. In particular, the determined position of the interventional device 5 may be shown overlaid on a registered pre-interventional image like a pre-interventional computed tomography image or magnetic resonance image of the person 2.

The interventional apparatus 1 described above with reference to FIGS. 1 to 8 can overcome problems with the handling of elongated medical devices like steerable devices, guide wires, catheters, et cetera in combination with optical shape sensing. In particular, the problem of entanglement of the devices and the possible disruption of optical shape sensing reconstruction, which may be caused by the entanglement, can be overcome. Entanglement is a serious issue, because during an interventional procedure many different medical devices may be used simultaneously, especially in complex endovascular interventions.

The interventional instrument and the optical fiber exit the handle axially, in order to prevent errors in the shape reconstruction of the optical shape sensing fiber and to provide proper interventional instrument handling, in particular, guide wire handling. For optimum performance the guides for the interventional instrument and the optical shape sensing fiber guide them such that they are as straight as possible within the handle. The optical shape sensing fiber and the interventional instrument leave the handle at substantially the same position. This implies that the proximal openings of the handle are close to each other, because the optical shape sensing fiber and the interventional instrument are guided through the handle relatively straight and as parallel as possible to each other and substantially along a same axis being the same as the axis of the proximal shaft of the steerable interventional device. This configuration reduces pressure and friction and can avoid a difficult advancement of both, the interventional instrument and the optical shape sensing fiber, and thereby avoid poor shape reconstruction of the interventional device. The proximal openings of the handle, through which the optical shape sensing fiber and the interventional instrument are guided, are preferentially close to an axial central line of the handle, in order to have a compact device and in order to minimize a possible motion of the optical shape sensing fiber and the interventional instrument proximal to the handle upon rotation of the handle. The optical shape sensing fiber and the guide wire are preferentially guided such through the handle that the interventional instrument can be advanced through the handle while minimizing the likelihood of contacting the optical shape sensing fiber. It is assumed that a user will advance the guide wire by using his thumb and index finger. The spacing between the two proximal openings from center line to center line is preferentially within a range of 10 to 15 mm.

The interventional apparatus may allow for an optical shape sensing reconstruction, i.e. a determination of the position of the interventional device within the person by optical shape sensing, without being disturbed by strong curves, bending and pressure. The proximal exits of the interventional instrument and of the optical shape sensing fiber at the handle are preferentially arranged at the respective most proximal part of the handle. Thus, the exit for the optical shape sensing fiber is positioned as far as possible, i.e. as proximal as possible, without having small radii of curvature from the shaft of the steerable interventional device to the proximal exit for the optical shape sensing fiber at the handle. The interventional instrument is preferentially positioned in a substantially straight line from the shaft of the interventional device, i.e. from the distal portion of the handle, to the proximal exit at the handle, i.e. to the second proximal opening. If these exit positions had been more distal, the likelihood of getting intertwined elements would increase, thereby reducing the easiness of handling these elements and increasing the likelihood of disturbing the optical shape sensing determination during an interventional procedure. The interventional apparatus is preferentially adapted to use steerable interventional devices in minimally invasive interventions, wherein guide wire guidance and guide wire steering is preferentially supported. However, instead of the guide wire other elongated medical devices, especially minimally invasive devices, can be used.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention relates to an interventional apparatus comprising an interventional device with a handle. The handle comprises a) a first guide for guiding an optical fiber, which is also guided within the interventional device, from a first proximal opening of the handle to a distal portion of the handle, wherein the first guide only has radii of curvature being larger than 10 mm, and b) a second guide for guiding an elongated interventional instrument from a second proximal opening of the handle to the distal portion of the handle. Since the first guide is relatively straight, the optical fiber is substantially not bent or only slightly bent and the likelihood that the interventional instrument and the optical fiber press against each other can be significantly reduced. This allows for an improved accuracy of determining the position of the interventional device by optical shape sensing.

The invention claimed is:

1. An interventional apparatus for performing an interventional procedure, the interventional apparatus comprising:
   an elongated interventional device comprising a first lumen accommodating an optical shape sensing fiber for allowing determination of a position of the elongated interventional device by optical shape sensing, and a second lumen for accommodating an elongated interventional instrument;
   an optical shape sensing device for determining the position of the elongated interventional device by optical shape sensing using the optical shape sensing fiber; and
   a handle comprising a) a first guide for guiding the optical shape sensing fiber, which is also guided within the elongated interventional device, from a first proximal opening of the handle to a distal portion of the handle, wherein the distal portion of the handle is adapted to be connected to a proximal portion of the elongated interventional device, and b) a second guide for guiding the elongated interventional instrument from a second proximal opening of the handle to the distal portion of the handle, wherein portions of the first guide and the second guide close to the first proximal opening and the second proximal opening are parallel to each other,
   wherein the elongated interventional device and the handle are attached to each other such that the optical shape sensing fiber is guided from the first proximal opening of the handle to the distal portion of the handle and then into the first lumen of the elongated interventional device and such that the elongated interventional instrument is guidable from the second proximal opening of the handle to the distal portion of the handle and then into the second lumen of the elongated interventional device.

2. The interventional apparatus as defined in claim 1, wherein the first guide only has radii of curvature larger than 100 mm.

3. The interventional apparatus as defined in claim 1, wherein the second guide only has radii of curvature larger than 300 mm.

4. The interventional apparatus as defined in claim 1, wherein the first guide and/or the second guide is formed by a tube extending from the respective first and/or second proximal opening of the handle towards the distal portion of the handle.

5. The interventional apparatus as defined in claim 1, wherein the handle comprises an elongated body having a distal opening at the distal portion of the handle for accommodating a distal accommodation element for accommodating the proximal portion of the elongated interventional device.

6. The interventional apparatus as defined in claim 5, wherein the elongated body has a first proximal body opening to which an elongated extension element is attached having a proximal extension element opening forming the first proximal opening of the handle, wherein the first guide is adapted to guide the optical shape sensing fiber from the proximal extension element opening through the first proximal body opening to the distal portion of the handle, wherein the extension element is made of a material being more flexible than a material of which the distal accommodation element is made.

7. The interventional apparatus of claim 5, wherein the elongated body has a second proximal body opening forming the second proximal opening of the handle such that the second guide guides the elongated interventional instrument from the second proximal body opening to the distal portion of the handle.

8. The interventional apparatus as defined in claim 1, wherein longitudinal axes of the handle and the proximal portion of the elongated interventional device are arranged in the same direction.

9. The interventional apparatus as defined in claim 1, wherein the first guide only has radii of curvature larger than 10 mm.

10. The interventional apparatus of claim 1, further comprising the optical shape sensing fiber and a tube into which the optical shape sensing fiber is embedded, wherein the tube is at least partially disposed outside of the handle.

11. An interventional apparatus for performing an interventional procedure, the interventional apparatus comprising:
an elongated interventional device comprising a first lumen accommodating an optical shape sensing fiber for allowing determination of a position of the elongated interventional device by optical shape sensing, and a second lumen for accommodating an elongated interventional instrument;
an optical shape sensing device for determining the position of the elongated interventional device by optical shape sensing using the optical shape sensing fiber; and
a handle comprising a) a first guide for guiding the optical shape sensing fiber, which is also guided within the elongated interventional device, from a first proximal opening of the handle to a distal portion of the handle, wherein the distal portion of the handle is adapted to be connected to a proximal portion of the elongated interventional device, and b) a second guide for guiding the elongated interventional instrument from a second proximal opening of the handle to the distal portion of the handle, wherein portions of the first guide and the second guide close to the first proximal opening and the second proximal opening are parallel to each other,
wherein the elongated interventional device and the handle are attached to each other such that the optical shape sensing fiber is guided from the first proximal opening of the handle to the distal portion of the handle and then into the first lumen of the elongated interventional device and such that the elongated interventional instrument is guidable from the second proximal opening of the handle to the distal portion of the handle and then into the second lumen of the elongated interventional device,
wherein the spacing between the first proximal opening and the second proximal opening from center line to center line is within a range of 10 to 15 mm.

12. The interventional apparatus of claim 11, further comprising the optical shape sensing fiber and a tube into which the optical shape sensing fiber is embedded, wherein the tube is at least partially disposed outside of the handle.

13. The interventional apparatus as defined in claim 11, wherein the handle comprises an elongated body having a first proximal body opening to which an elongated extension element, made of a material being more flexible than a material of which the elongated body is made, is attached having a proximal extension element opening forming the first proximal opening of the handle, the first guide being adapted to guide the optical shape sensing fiber from the proximal extension element opening through the first proximal body opening to the distal portion of the handle.

14. The interventional apparatus as defined in claim 13, wherein the elongated body has a second proximal body opening forming the second proximal opening of the handle such that the second guide guides the elongated interventional instrument from the second proximal body opening to the distal portion of the handle.

15. The interventional apparatus as defined in claim 11, wherein at least one of the first guide and the second guide is formed by a tube extending from the respective first or second proximal opening of the handle towards the distal portion of the handle.

16. The interventional apparatus as defined in claim 11, wherein at least one of the first guide and the second guide is formed by a tube extending from the respective first or second proximal opening of the handle towards the distal portion of the handle.

17. An interventional apparatus for performing an interventional procedure, the interventional apparatus comprising:
an elongated interventional device comprising a first lumen accommodating an optical shape sensing fiber for allowing determination of a position of the elongated interventional device by optical shape sensing, and a second lumen for accommodating an elongated interventional instrument;
an optical shape sensing device for determining the position of the elongated interventional device by optical shape sensing using the optical shape sensing fiber; and
a handle comprising a) a first guide for guiding the optical shape sensing fiber, which is also guided within the elongated interventional device, from a first proximal opening of the handle to a distal portion of the handle, wherein the distal portion of the handle is adapted to be connected to a proximal portion of the elongated interventional device, and b) a second guide for guiding the elongated interventional instrument from a second proximal opening of the handle to the distal portion of the handle, wherein portions of the first guide and the second guide close to the first proximal opening and the second proximal opening are parallel to each other,
wherein the elongated interventional device and the handle are attached to each other such that the optical shape sensing fiber is guided from the first proximal opening of the handle to the distal portion of the handle and then into the first lumen of the elongated interventional device and such that the elongated interventional instrument is guidable from the second proximal opening of the handle to the distal portion of the handle and then into the second lumen of the elongated interventional device, and
wherein the handle comprises an elongated body having a first proximal body opening to which an elongated extension element, made of a material being more flexible than a material of which the elongated body is made, is attached having a proximal extension element opening forming the first proximal opening of the handle, the first guide being adapted to guide the optical shape sensing fiber from the proximal extension element opening through the first proximal body opening to the distal portion of the handle.

18. The interventional apparatus as defined in claim 17, wherein the elongated body has a second proximal body opening forming the second proximal opening of the handle such that the second guide guides the elongated interventional instrument from the second proximal body opening to the distal portion of the handle.

19. The interventional apparatus of claim 17, further comprising the optical shape sensing fiber and a tube into which the optical shape sensing fiber is embedded, wherein the tube is at least partially disposed outside of the handle.

20. A position determination method for determining a position of the elongated interventional device of the interventional apparatus as defined in claim 1, the position determination method comprising determining the position by optical shape sensing by using the optical shape sensing device and the optical shape sensing fiber guided from the first proximal opening of the handle to the distal portion of the handle and then into the first lumen of the interventional device.

\* \* \* \* \*